United States Patent [19]

Negoro et al.

[11] Patent Number: 5,301,656
[45] Date of Patent: Apr. 12, 1994

[54] ENDOSCOPE

[75] Inventors: Daisaku Negoro; Hisao Yabe; Hideo Ito; Yoshihiro Iida; Ichiro Nakamura; Akira Suzuki; Yoshinao Oaki; Koji Koda, all of Tokyo, Japan

[73] Assignee: Olympus Optical Co., Ltd., Tokyo, Japan

[21] Appl. No.: 864,490

[22] Filed: Apr. 7, 1992

[30] Foreign Application Priority Data

Apr. 19, 1991 [JP] Japan ................. 3-116976

[51] Int. Cl.$^5$ .............................................. A61B 1/00
[52] U.S. Cl. .................................................... 128/4
[58] Field of Search .................... 128/4; 134/135; D23/259, 261, 266, 267, 387, 391; D24/137, 138

[56] References Cited

U.S. PATENT DOCUMENTS

| D. 244,033 | 4/1977 | Elson | D23/266 |
|---|---|---|---|
| D. 259,950 | 7/1981 | Henry | D23/259 |
| D. 310,259 | 8/1990 | Hitchins | D23/267 |
| 4,064,886 | 12/1977 | Heckele | 134/184 X |
| 4,299,244 | 11/1981 | Hirai | 134/199 X |
| 4,637,378 | 1/1987 | Sasa | 128/4 A |
| 4,748,993 | 6/1988 | Llewellyn | 134/135 X |
| 4,825,850 | 5/1989 | Opie et al. | |
| 4,878,484 | 11/1989 | Miyagi | 128/4 |
| 4,928,699 | 5/1990 | Sasai | 128/4 X |
| 4,982,724 | 1/1991 | Saito et al. | 128/4 |
| 5,007,406 | 4/1991 | Takahashi et al. | |

FOREIGN PATENT DOCUMENTS

| 3-76127 | 12/1991 | Japan . | |
| 2149884 | 6/1985 | United Kingdom | 128/4 |

Primary Examiner—Richard J. Apley
Assistant Examiner—Karen A. Jalbert
Attorney, Agent, or Firm—Frishauf, Holtz, Goodman & Woodward

[57] ABSTRACT

An endoscope comprises a control section at an operator side, a plurality of operation knobs projected at the control section, an insertion section insertable into a human body cavity for medical treatment and having a proximal end connected to the control section and distal end section insertable into the body cavity, and a water drain guide member provided at the respective operation knob of the control section and being of such a type that, after an endoscope body has been washed, the guide member can guide deposited water on the recess of the respective knob in a direction to run and drain therealong, when the control section is horizontally located with the operation knob set in a normally upward state.

12 Claims, 9 Drawing Sheets

ENDOSCOPE

BACKGROUND OF THE INVENTION

1. Field of the Invention

The present invention relates to an endoscope which can be cleaned by being washed with water.

2. Description of the Related Art

Generally, an endoscope, once being used for treatment, has been washed and sterilized by a washing/sterilizing device and rinsed with water, etc. The washed endoscope, upon being thoroughly dried, is stored in a special storage site for endoscopes.

Since, at that time, pools of water are left locally on the surface of the endoscope due to the complicated surface configuration of the endoscope, it takes a relatively long time to fully dry the whole endoscope after being washed.

The endoscope, if being thoroughly not dried after being washed with water, involves an increase in various germs in pools of water on the outer surface of the endoscope. Therefore, there is a risk that the outer surface of the endoscope will be re-contaminated with various germs.

In order to prevent this problem, a very time-consuming operation is required to positively dry the endoscope surface in a longer period of time. There is, therefore, a growing demand that the endoscope be dried efficiently.

SUMMARY OF THE INVENTION

It is accordingly the object of the present invention to provide an endoscope which, after being washed, can be efficiently dried in a brief period of time.

In order to achieve the aforementioned object, an endoscope is provided which comprises a control section at an operation-end side, a plurality of members projecting at the control section, and an insertion section insertable in at least one of a human body cavity or duct for medical treatment and an industrial pipe or duct and having a proximal end connected to the control section and a distal end portion insertable into the duct, wherein a water drain guide means is provided on the respective projecting member of the control section and can be placed in at least one, uniformly oriented, direction of the control section to, after an endoscope body has been washed, allow water which is deposited on the respective projecting member to be run and drain dropwise.

According to the present invention, it is possible to, after the endoscope body has been washed, effectively dry its component parts in a brief period of time and positively prevent re-contamination of the endoscope which may be caused by various germs in a pool of water on the surface of the endoscope.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

One embodiment of the present invention will be explained with reference to the accompanying drawings below.

Figure 2:
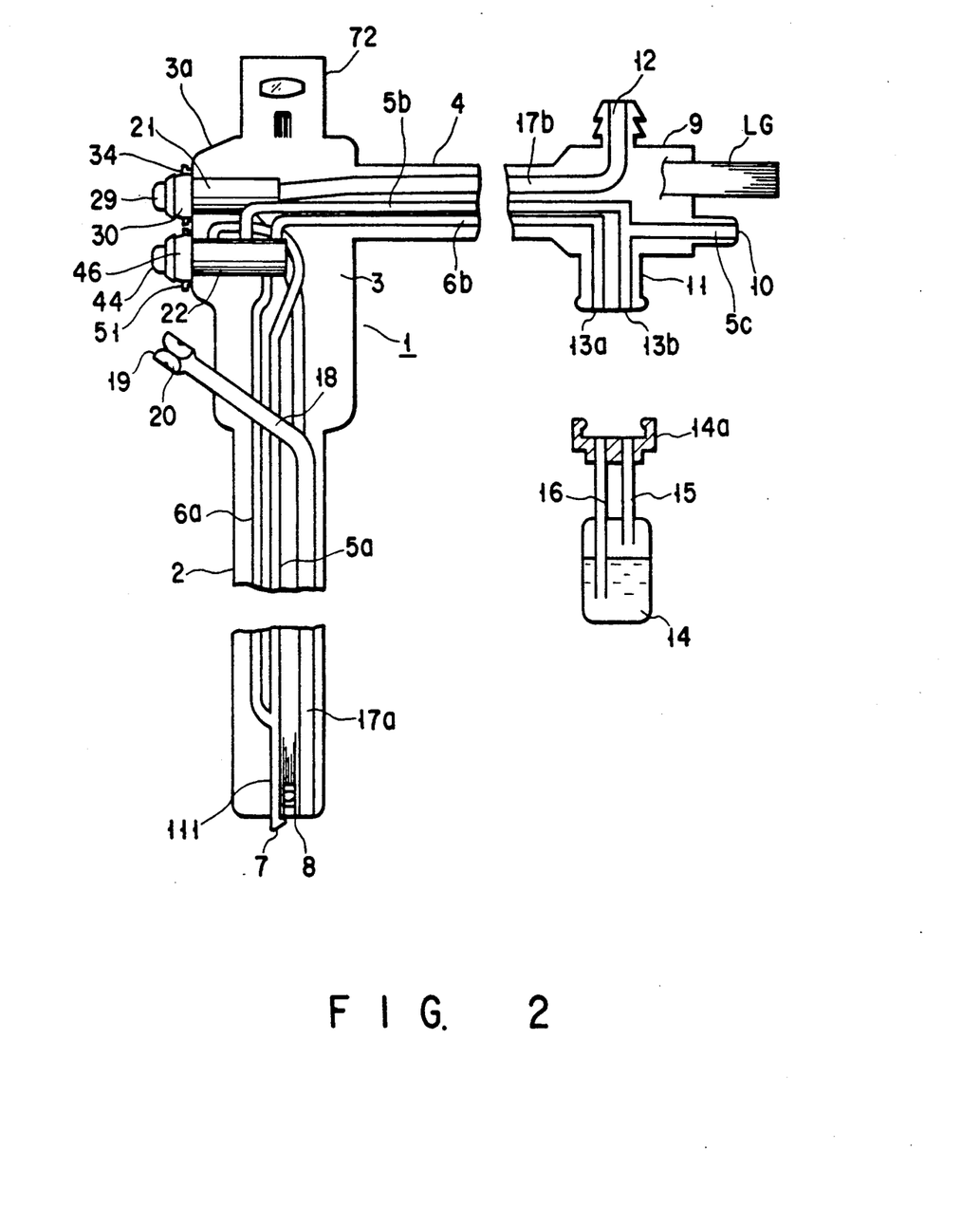
FIG. 2 is a diagrammatic view showing an arrangement of inner tube passages for the endoscope.

In FIG. 2, reference numeral 1 shows an endoscope. The endoscope 1 has an insertion section 2 to be inserted into, for example, a cavity or duct of a living body, etc., or an industrial duct or pipe, such as gas pipes, an operator-side control section 3 and a universal cord 4 connected at a base end to the control section 3.

A tip construction unit is connected to a distal end of an insertion section 2 via a bendable section, not shown, which can be bent in the up/down and right/left directions.

The control section 3 is equipped with a first operation knob 73 for enabling the bendable section of the insertion section 2 to be operated in the right/left direction, a second operation knob 74 for enabling the bendable section to be operated in the up/down direction, a suction button 29, an air/water supply button 44, a forceps introducing connector 19, a grip section 71, an eyepiece section 72, etc.

The first operation knob 73 is fixed to the forward end of a first rotation shaft rotatably mounted on the control section 3. The second operation knob 74 is fixed to the forward end of a second rotation shaft mounted coaxial with the first rotation shaft.

An operation wire pulling mechanism is connected to the base ends of the first and second rotation shafts so as to controllably operate the bendable section of the insertion section 2. The rotation operation of the first operation knob 73 enables the corresponding operation wire to be pulled via the corresponding pull mechanism so that the bendable section of the insertion section 2 is controllably operated in the right/left direction. Similarly, the rotation operation of the second operation knob 74 enables the corresponding operation wire to be pulled via the corresponding pull mechanism so that the bendable section of the insertion section is controllably operated in the up/down direction.

A cylindrical diopter adjusting member 75 is rotatably mounted on the eyepiece section 72 so as to adjust the diopter of the eyepiece section 72.

A connector section 9 connected to an optical device, not shown, is connected to the forward end of the universal cord 4. The incident end of a light guide LG in the endoscope 1 is projected on the connector section 9.

In the use of the endoscope 1, the connector section 9 is connected to a light source unit. In this state, illumination light is transmitted from a light source in the light source unit to the light incident end face of the light guide LG.

The light guide LG is made up of a light fiber bundle. Illumination light supplied to the incident end face of the light guide LG from the light source unit is transmitted to the distal-end side of the light guide LG through the light fibers of the light guide LG.

An exit end section, not shown, is provided on the distal-end side of the light guide LG and fixed to the distal construction unit on the distal end of the insertion section 2. The illumination light transmitted through the light fibers of the light guide LG exits from the exit-end face, that is the distal end face of the exit-end face, toward a foreground object.

An observation window 8 is mounted, in a watertight fashion, on the distal construction unit, that is, on a nearly central area of the distal construction unit. The exit-end face of the light guide LG, distal open end to an upstream-side suction tube 17a and injection nozzle 7 are situated around the area of the observation window 8 in which case the suction tube 17a serves also as a treating unit insertion channel.

A downstream-side air supply tube 5a, downstream-side water supply tube 6a and upstream-side suction tube 17a are provided in the insertion section 2.

The distal end sides of the downstream-side water supply tube 6a and downstream-side air supply tube 5a are joined into a single common air/water supply tube 111 in the neighborhood of the distal end of the insertion section. The distal end of the air/water supply tube 111 is connected to the air/water supply nozzle 7. In the use of the endoscope 1, the outer surface of the observation window 8 is blown or injected with air supplied via the air/water supply nozzle 7 or with a liquid, such as washing water, supplied via the air/water supply nozzle 7.

The base- or proximal-end side of the upstream side suction tube 17a is connected through a suction switching valve 21 in the control section 3 to a downstream-side suction tube 17b provided in the universal cord 4.

The base-end sides of the downstream-side air supply tube 5a and downstream-side water supply tube 6a are connected through an air/water supply switching valve 22 in the control section 3 to the upstream-side air supply tube 5b and upstream-side water supply tube 6b, respectively.

Figure 3:
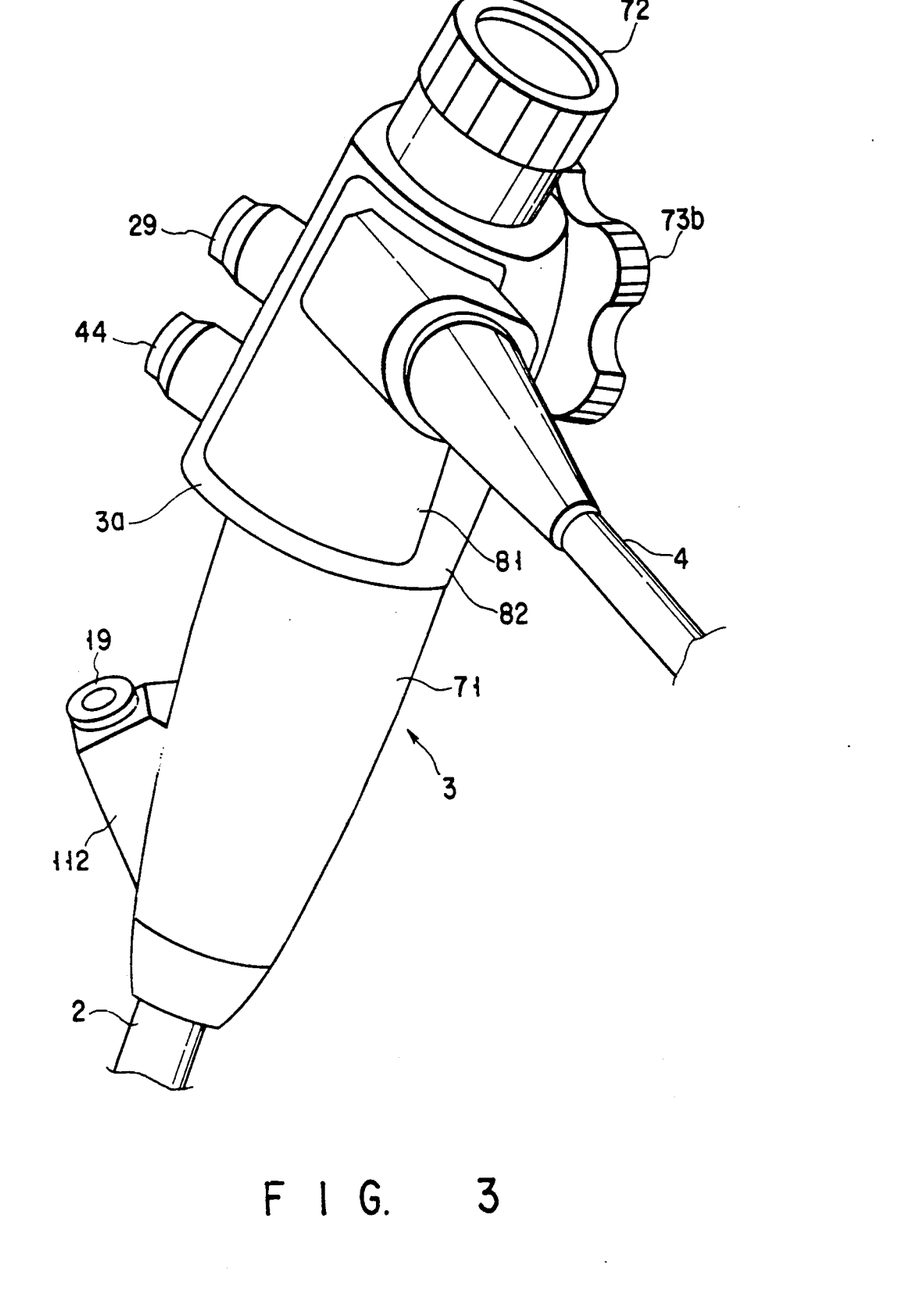
FIG. 3 is a perspective view showing the control section of the endoscope.

A treating unit insertion channel 18 is branched off from the tube 17a in the upstream side thereof by a Y-bend. A mouth piece 19 is fitted to the base end of the channel 18. The mouth piece 19 is mounted to a projection 112 protruded from the grip section 71 of the control section 3 as shown in FIG. 3. A seal member 20 made of an elastic material is detachably mounted, as shown in FIG. 2, to the open end of the mouth piece 19.

The outer end of a narrow tube-like air supply connector section 10 is connected to a forward end side of the connector section 9 on the forward end of the universal cord 4. The outer ends of the air/water supply connector section 11 and suction connector section 12 are connected to the outer surface portion of the connector section 9. These outer ends of the connector sections 10, 11 and 12 are projected from the surface of the control section 3.

A water supply port 13a and air supply port 13b are provided in the air/water supply connector section 11. The water supply port 13a and air supply port 13b are connected to the base ends of the upstream-side water supply tube 6b and upstream-side air supply tube 5b, respectively.

One end of a branched tube 5c is connected to the base end side of the upstream-side air supply tube 5b. The other end of the branched tube 5c is connected to the inner end of the air supply connector section 10.

An outside water supply tank 14 is detachably connected by a coupling means 14a to the air/water supply connector section 11.

The upper ends of an air supply tube 15 and water supply tube 16 are connected to the coupling means 14a. The lower ends of the air supply tube 15 and water supply tube 16 are connected to the water supply tank 14 side. The lower end portion of the water supply tube 16 extends into a zone near the inner bottom of the water supply tank 14 and is immersed in washing water in the water supply tank 14. The lower end of the air supply tube 15 is situated in an upper zone in the water supply tank 14.

When the coupling means 14a is to be connected to the air/water connector section 11, the air supply port 13b and water supply port 13a are connected to the air supply tube 15 and water supply tube 16, respectively, which are provided on the coupling means 14a side. When, in this state, air is supplied through the air supply tube 15 into the water tank 14, pressure is applied to air in the water supply tank 14.

The base end of the downstream-side suction tube 17b is connected to the inner end of the suction connector section 12. A suction pump, not shown, as well as a suction tube connected to a suction bottle is detachably connected to the outer end of the suction connector section 12.

With the connector section 9 coupled to the light source device, the connector section 10 of the connector section 9 is connected to an air supply pump, not shown, in the light source device. The air coming from the supply pump is conducted from the air supply connector section 10 via the branched tube 5c to the upper-side air supply-tube 5b side or the air supply port 13b side of the air/water supply connector section 11.

Figure 4:
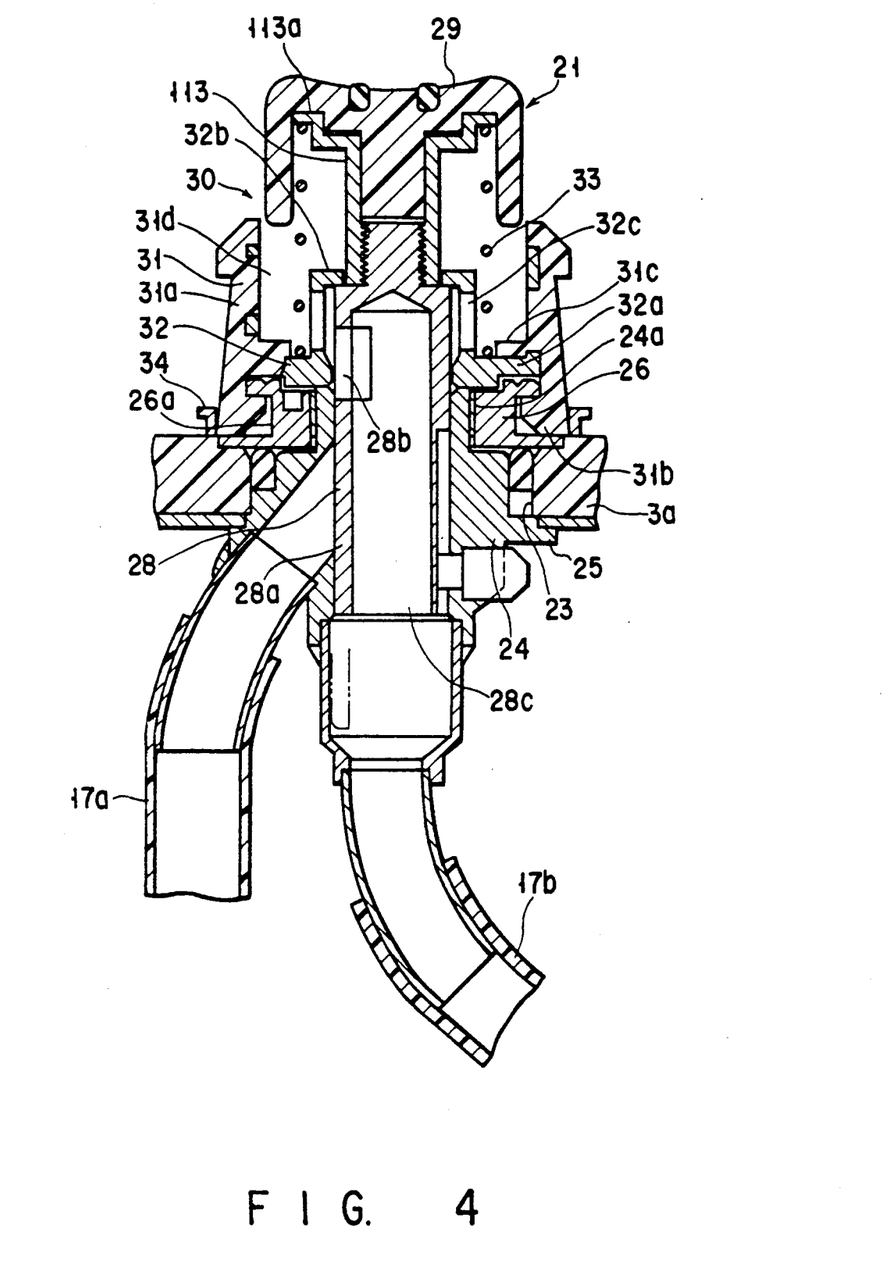
FIG. 4 is a longitudinal cross-sectional view showing a suction switching valve.

FIG. 4 shows the inner arrangement of the suction switching valve 21. A suction cylinder 24 is provided in the suction switching valve 21 such that it is inserted into a mount hole 23 provided in a casing 3a of the control section 3.

An externally threaded mount section 24a is provided on the forward end portion of the suction cylinder 24. A fixed flange 25 is formed on the outer periphery of the suction cylinder 24 such that it has a diameter greater than that of the mount hole 23.

The fixed flange 25 is fitted into the mount hole 23 provided in the casing 3a and, in this case, the threaded mount section 24a of the forward-end side of the suction cylinder 24 is externally projected through the mount hole 23. A cylinder connector 26 is placed on the outer side of the casing 3a and has a diameter greater than the mount hole 23. The connector 26 is threadably fixed to the threaded mount section 24a of the suction cylinder 24. By so doing, the suction cylinder 24 is fixed to the inner wall of the mount hole 23 in the casing 3a.

The forward end portion of the downstream-side suction tube 17b is connected to the base-end side of the suction cylinder 24. The base end of the upstream-side suction tube 17a is connected to the outer periphery of the suction cylinder 24.

A ring-like suction button unit mount groove 26a is formed on the outer periphery of the cylinder connector 26. The suction button unit 30 is detachably fitted into the mount groove 26a of the connector 26.

The suction button unit 30 includes a suction piston 28 for passage switching in the suction cylinder 24, a suction button 29, a suction button mount rubber 31, support member 32, a return spring 33, etc.

A bottomed-cylindrical piston body 28a is provided at the suction piston 28. A passage hole 28b is provided on the cylindrical wall of the piston body 28a. The suction piston 28 is slidably mounted in the suction cylinder 24 with an open end 28c down.

The closed end side of the suction piston 28 extends from the open end of the suction cylinder 24 toward an upper side as viewed in FIG. 4. The suction button 29 is connected by a cylindrical coupling member 113 to the closed end of the suction piston 28. A flange-like spring seat 113a is provided on the upper end portion of the coupling member 113 as shown in FIG. 4.

A cylindrical unit 31a is provided on the suction button mount rubber 31 and an engaging hook 31b is provided on the inner wall of the base-end side of the cylindrical body 31a. The hook 31b is detachably fitted into the mount groove 26a of the cylinder connector 26.

A fixed projection 31c is provided partway to the inner wall surface of the cylinder body 31a so as to fixedly hold the support member 32 in place.

On the upper side of the fixed projection 31c, a recess 31d is provided at the inner wall of the cylindrical body 31a. The recess 31d holds the suction button 29 therein such that the suction button 29 can be projected. The recess 31d is opened to the outer atmosphere.

The support member 32 is formed of a substantially cylindrical member and supports the suction piston 28 and suction button 29 such that they are movable in the axial direction of the suction cylinder 24. The support member 32 has a flange-like spring seat section 32a at its base end, a suction piston stopper 32b at its forward end and an outer air introducing inlet 32c at its outer periphery.

The return spring 33 is disposed between the spring seat section 113a of the coupling member 113 and the spring seat section 32a of the support member 32.

The suction switching valve 21 holds the suction button 29 in place such that it is normally projected out of the recess 31d of the cylindrical body 31a under the action of the return spring 33 as shown in FIG. 4. At this time, the suction piston 28 is held in a state to abut against the stopper 32b of the support member 32. In this state, the passage hole 28b of the suction piston 28 is connected to an outer air introducing inlet 32c in the support member 32 and the upstream-side suction tube 17a is held in an non-sucked state.

When the suction button 29 is pushed against the action of the return spring 33, the suction button 29 is moved down into the recess 31d of the cylindrical body 31a so that it is stored in a storage position. At this time, the suction button 29 and suction piston 28 are pushed down to a position where the passage hole 28b of the suction piston 28 is coupled to the upstream-side suction tube 17a. When this is done, the passage hole 28b of the suction piston 28 is connected to the upstream-side suction tube 17a so that the upstream-side suction tube 17a is switched to a suction mode.

In this way, the suction button 29 of the suction switching valve 21, when being operated, can be switched to a suction mode of the upstream-side suction tube 17a.

Figure 5:
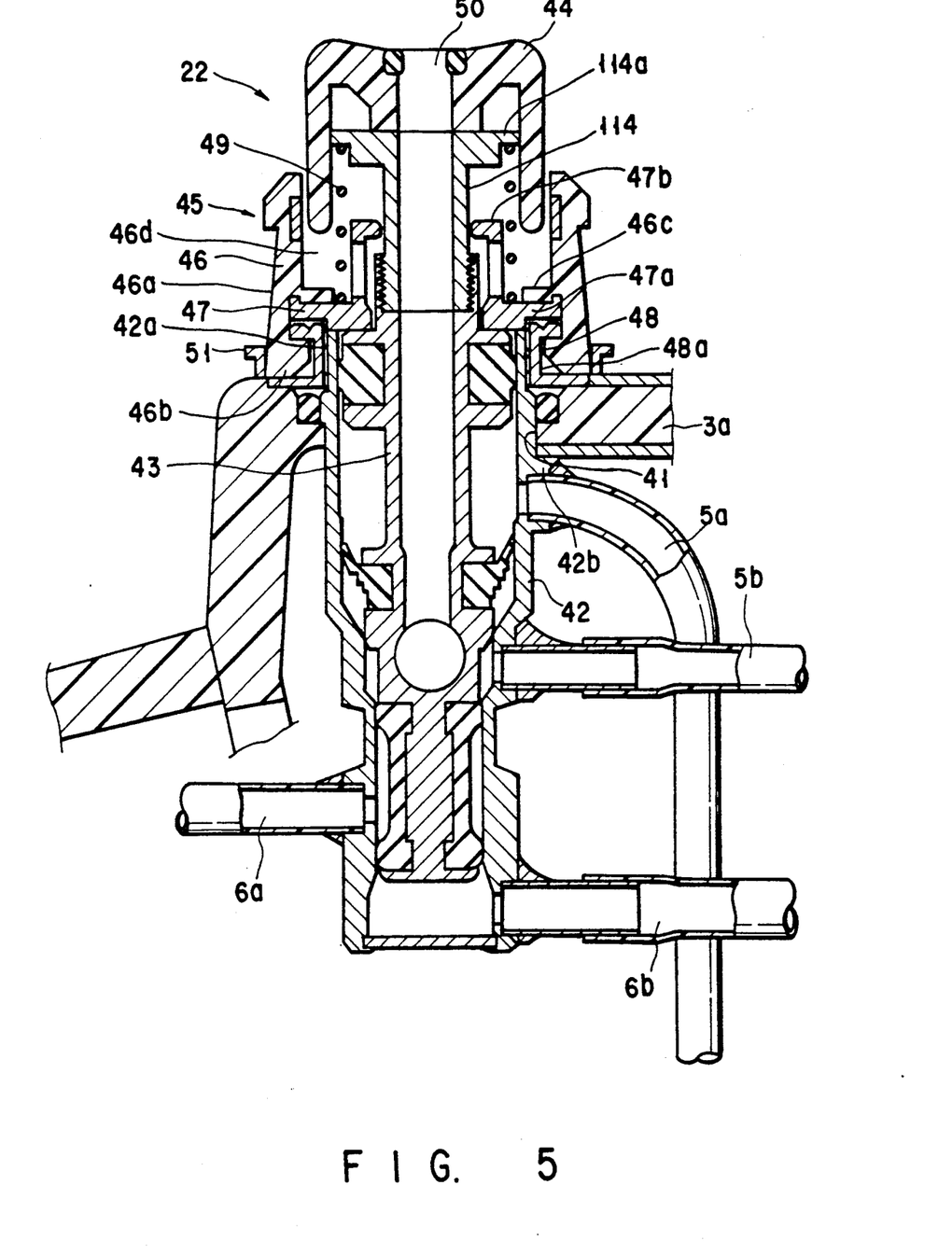
FIG. 5 is a longitudinal cross-sectional view showing an air/water supply switching valve.

FIG. 5 shows an inner arrangement of the air/water supply switching valve 22.

A cylindrical air/water supply cylinder 42 is disposed at the air/water supply switching valve 22 such that it is inserted into a mount hole 41 in the casing 3a.

An externally threaded mount section 42a is provided on the forward end portion of the air/water support cylinder 42. A fixed flange 42b is provided on the outer periphery of the air/water supply cylinder 42 and has a diameter greater than that of the mount hole 41.

The fixed flange 42b is joined to the inner wall of the mount hole 41 in the casing 3a and, in this state, the externally threaded section 42a on the forward end side of the air/water supply cylinder 42 is projected out of the mount hole 41. A cylinder connector 48 whose diameter is greater than that of the mount hole 41 is disposed outside the casing 3a and threadably fixed to the externally threaded section 42a of the cylinder 42. By so doing, the air/water supply cylinder 42 is fixed to the inner wall of the mount hole 41 of the casing 3a.

The base end of the downstream-side air supply tube 5a, base end of the downstream-side water supply tube 6a, forward end of the upstream-side air supply tube 5b and forward end of the upstream-side water supply tube 6b are connected to the outer periphery of the air/water supply cylinder 42.

A ring-like air/water supply button unit mount groove 48a is provided on the outer periphery of a cylinder connector 48. The air/water supply button unit 45 is detachably mounted on the mount groove 48a of the cylinder connector 48.

An air/water supply button unit 45 includes an air/-water supply piston 43 for cylinder passage switching, an air/water supply button 44, an air/water supply button mount rubber 46, support member 47, a return spring 49, etc.

The air/water supply piston 43 is so provided as to be slidable in the air/water supply cylinder 42. A head of the air/water supply piston 43 extends via the forward open end of the air/water supply cylinder 42 toward the upper side as viewed in FIG. 5.

The air/water supply button 44 is connected by the air/water supply button 44 to the head of the air/water supply piston 43. The coupling member 114 has a flange-like spring seat section 114a at its upper end as viewed in FIG. 5.

A cylindrical body 46a is provided at the air/water supply button mount rubber 46. An engaging hook 46b is projected on the inner wall of the base end of the cylindrical body 46a. The engaging hook 46b is detachably engaged with a mount groove 48a of the cylinder connector 48.

A fixed, inwardly extending projection 46c fixes the support member 47 to an area partway of the inner wall of the cylindrical body 46a. At the upper side of the cylindrical body 46a to store the air/water supply button 44 in a manner to enable it to be projected.

The support member 47 is made up of a substantially cylindrical member and movably support the air/water supply piston 43 and air/water supply button 44 in the axial direction of the air/water supply cylinder 42. The support member 47 has a flange-like spring seat section 47a at its base and a piston stopper 47b at its forward end.

The return spring 49 is disposed between the spring seat section 114a of the coupling member 114 and the spring seat section 47a of the support member 47.

A leakage hole 50 is provided in the air/water supply piston 43 and air/water supply button 44.

The air/water supply switching valve 22 normally holds the air/water supply button 44 as shown in FIG. 5 such that it is projected out of the recess 46d at the cylindrical body 46a under the action of the return spring 49. At this time, the air/water supply piston 43 is held in a state to abut against the stopper 47b of the support member 47. In this normal state, the air/water supply piston 43 allows a connection/ to be made between the upstream-side air/water supply tube 5b. and the leakage hole 50 and a connection to be made between the donwstream-side air supply tube 5a and the upstream-side air supply tube 5b through a check valve and shuts off a communication between the upstream-side water supply tube 6b and the downstream-side water supply tube 6a. In this state, air coming through the upstream-side air supply tube 5b leaks to an outside via the leakage hole 50.

When the leakage hole 50 of the air/water supply piston 43 is blocked by the operator finger, the air coming through the upstream-side air supply tube 5b enters the downstream-side air supply tube 5a side through a check valve and is supplied to the injection nozzle 7 so that an air supply operation is carried out.

When the air/water supply button 44 is pushed down against the action of the return spring 49 with the leakage hole 50 of the air/water supply piston 43 blocked by the operator finger, the button 44 is moved to a storage position where it is stored at the recess 46d of the cylindrical body 46a. At this time, the air/water supply button 44 and air/water supply piston 43 is set to a lower position, thus shutting off the supply of the air to the downstream-side air supply tube 5a side, while allowing a connection to be made between the upstream-side water supply tube 6b and the downstream-side water supply tube 6a. In this state, the liquid supplied from the upstream-side water supply tube 6b flows into the downstream-side water supply tube 6a and hence into the injection nozzle 7 so that a water supply operation is carried out.

The supply of the air and water to the injection nozzle 7 can be switchingly effected by operating the air/-water supply button 44 of the air/water switching valve 22.

On the casing 3a of the control section 3 are mounted the mount connector 34 (for tube passage washing) provided around the cylinder connector 26 for the suction cylinder 24 and the mount connector 51 (for tube passage washing) provided around the cylinder connector 48 for the air/water supply cylinder 42.

Figure 6:
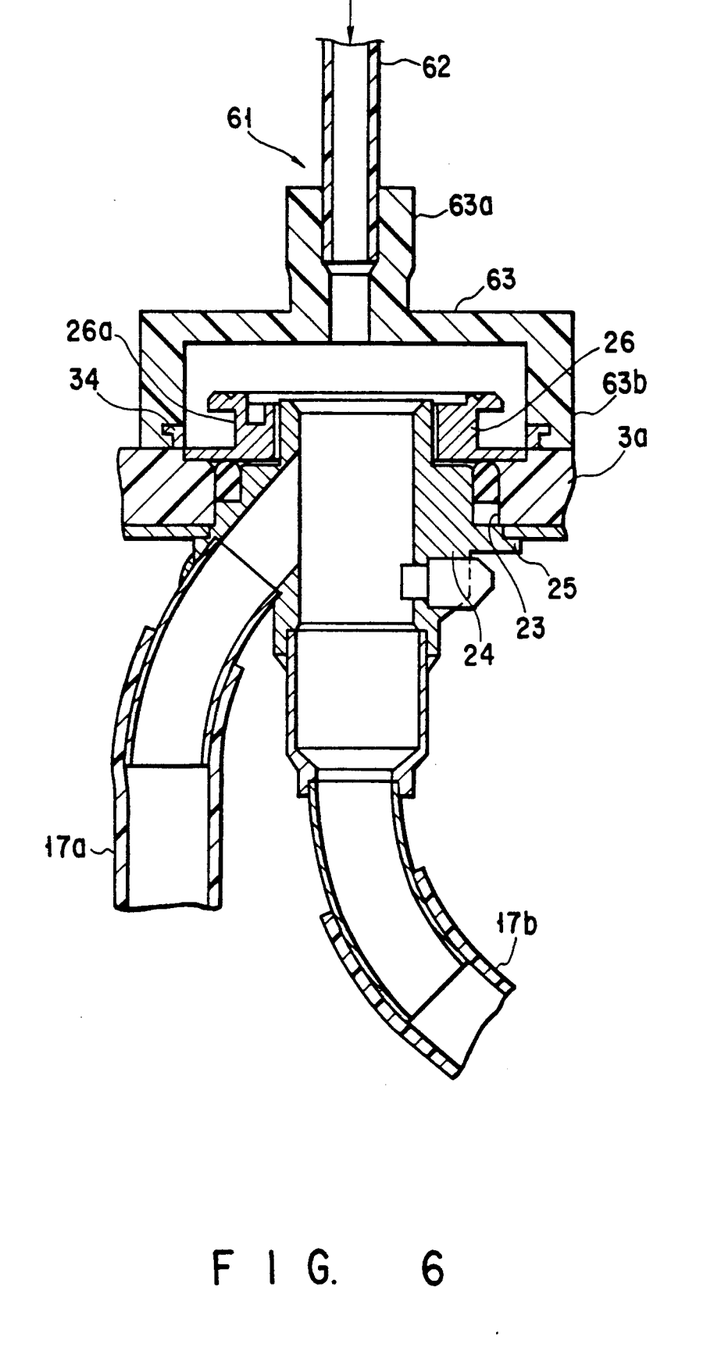
FIG. 6 is a longitudinal cross-sectional view showing a state in which a suction button unit is detached from a suction cylinder of the suction switching valve.
Figure 7:
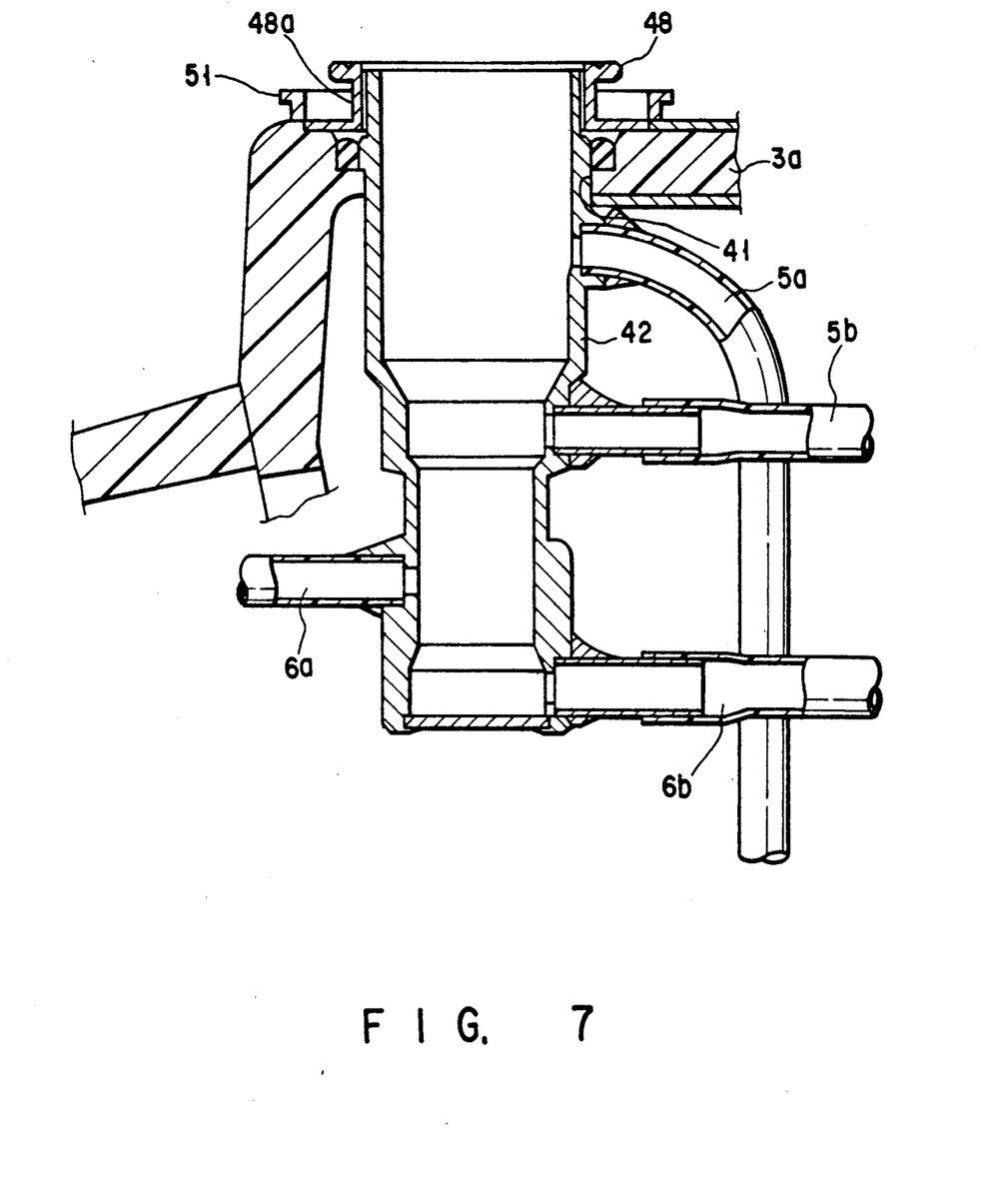
FIG. 7 is a longitudinal cross-sectional view showing a state in which an air/water supply button unit is removed from an air/water supply cylinder of an air/water supply switching valve.

A connector washing unit 61 is detachably mounted on the tube passage washing mount connector 34 and 51 as shown in FIG. 6 in such a state as to detach the suction button unit 30 and air/water supply button units 45 from the cylinder connectors 26 and 48, respectively, as shown in FIGS. 6 and 7.

A washing water supply tube 62 and connection connector 63 connected to the forward end of the washing water supply tube 62 are provided in the connection washing unit 61. The base end of the washing water supply tube 62 is connected to a washing water supply device, not shown.

A first connector section 63a of a small diameter connected to the washing water supply tube 62 is provided on one-end side of the connector 63, and a second connector section 63b of a larger diameter connected to the mount connector 34 or 51 is provided on the other end side of the connector 63. In this case, the mount connectors 34 and 51 are mounted properly in a spaced-apart relation one to the outside of the connector 26 of the suction cylinder 24 and one to the cylinder connector 48 of the air/water supply cylinder 42.

As shown in FIG. 6, for example, the connector 63 for the connector washing unit 61 is connected to the mount connector 34 with the suction button unit 30 detached from the cylinder connector 26 for the suction cylinder 24. By so doing, the cylinder connector 26 for the suction cylinder 24 is held within the connector 63 of the tube washing unit 61. In this state, therefore, a washing liquid is supplied to the connector 63 side through the washing water supply tube 62 of the tube washing unit 61 to enable it to be supplied to the whole cylinder connector 26. It is, therefore, possible to positively wash an inaccessible place or site, such as the outer periphery, etc., of the cylinder connector 26.

As shown in FIG. 7, with the air/water supply button unit 45 detached from the cylinder connector 48 for the air/water supply cylinder 42, the connector 63 of the tube washing unit 61 is connected to the mount connector 51, flowing a washing liquid around the whole cylinder connector 48 for the air/water supply cylinder 42 so that the cylinder connector 48 can be positively washed. An outer case body 82, control section cover 81 and hand grip section 71 are mounted on the casing 3a of the control section 3 as shown in FIG. 3.

Figure 1A:
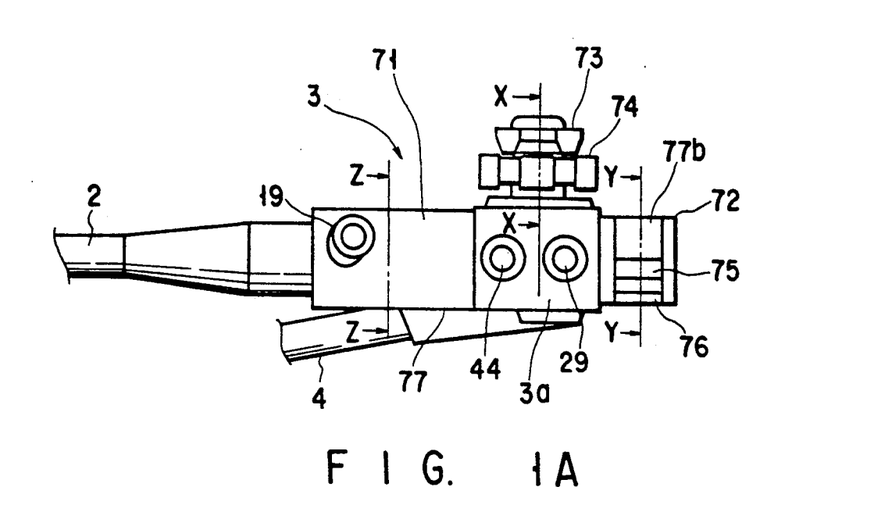
FIG. 1A is a side view diagrammatically showing a control section of an endoscope according to one embodiment of the present invention.

The suction button 29 of the suction switching valve 21, air/water supply button 44 of the air/water supply switching valve 22, first and second operation knobs 73 and 74, eyepiece section 72, etc. are mounted on the outer case body 82 as shown in Figs. 1A and 3.

The universal cord 4 is mounted on the control section cover 81 and the grip section 71 is provided on the insertion section 2 side of the control section 3.

Figure 8:
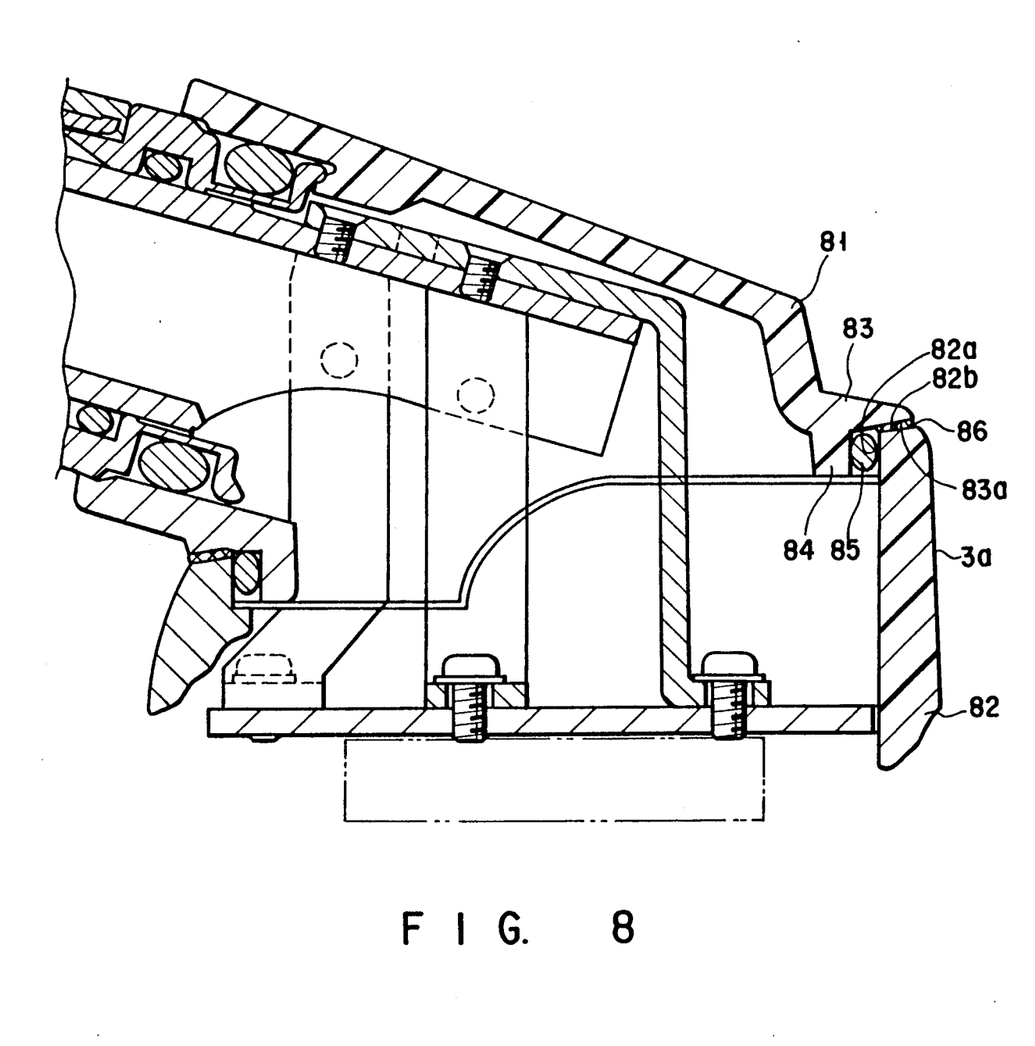
FIG. 8 is a longitudinal cross-sectional view showing a state of connection between an outer case body and a control section cover.

In this way, the grip section mount opening, as well as a control section's cover mount opening 82a as shown in FIG. 8, is provided on the outer case body 82.

A ring-like connection section 84 is provided at an area of connection to the control section cover mount opening 82a such that it is situated relative to the control section cover mount opening 82a.

An O-ring 85 is fitted between the control section cover mount opening 82a of the outer case body 82 and the outer periphery of the ring-like connection section 84 of a control section cover 81, thus sealing that area between the two.

A quick drying type silicone rubber adhesive 86 is filled between the end portion 82b of the cover mount opening 82a of the outer case body 82 and a connection face 83a of the connection area 83 on the control section cover 81 side. By so doing, it is possible to positively prevent any possible dirty deposit from being formed there.

In this case, the silicone rubber type adhesive 86 will have it bonded face relatively weakened in a direction that is perpendicular to the control section cover 81 and outer case body 82, that is, in a direction perpendicular to (that in which the control section cover 81 20 and outer case body 82 are bonded to each other), because these members 81 and 82 are made of plastic material. It is, therefore, possible to readily detach the control section cover 81 from the outer case body 82.

A plurality of water drain guide means 77a, 77b, 77c are provided for guiding water in a water-dropping direction which is deposited on the outer surface of the control section 3 after the endoscope body has been washed.

In this case, the endoscope 1, after being washed, is set in a horizontal state with the first and second operation knobs 73 and 74 up as shown in FIG. 1A.

Figure 1B:
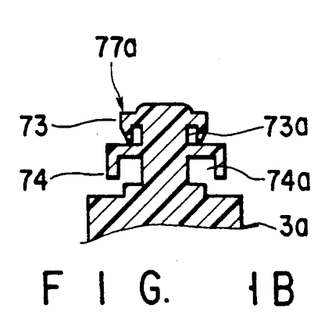
FIG. 1B is a cross-sectional view as taken along line X—X in FIG. 1A.

The first water drain guide means 77a is so set that those recesses 73a and 74a of the first and second operation knobs 73 and 74 are all oriented in a downfacing direction as shown in FIG. 1B. In that set position, any remaining water or a pool of water in the recesses 73a and 74a is fully drained along the outer surface of the casing 3a.

Figure 1C:
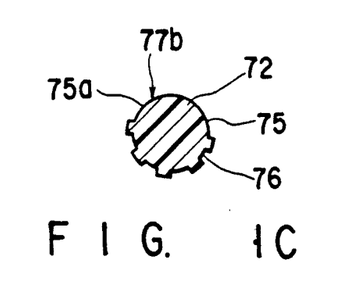
FIG. 1C is a cross-sectional view as taken along line Y—Y in FIG. 1A.

The second water drain guide means 77b has a plurality of ridges 76 only on the lower half section of the outer periphery of the diopter adjusting ring 75 of the eyepiece section 72 as shown in FIG. 1C so as to prevent a slippage. The drain guide means 77b has an even smooth surface 75a on the upper half section of the outer periphery of the ring 75. By so doing, pools of water deposited on the upper half of the outer periphery of the ring 75 is smoothly dropped along the outer periphery of the ring 75 and fully drained.

Figure 1D:
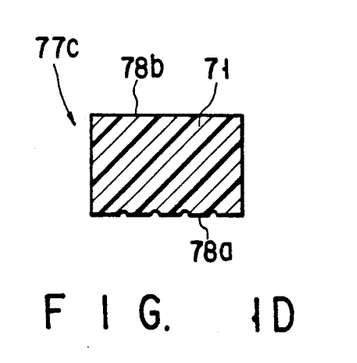
FIG. 1D is a cross-sectional view as taken along line Z—Z in FIG. 1A.

The third water drain guide means 77c has grooved surface 78a on the lower surface side of the grip section 71 as shown in FIG. 1D so as to prevent a slippage. The drain guide means 77c has a non-grooved smooth surface 78b on the upper side. By so doing, remaining water or a pool of water deposited on the upper surface side of the grip section 71 is smoothly run along the upper end side surfaces of the grip section 71 and fully drained.

Since the first to third water drain guide means 77a, 77b and 77c are provided on the control section 3 of the endoscope, it is possible to smoothly drop the water off the outer surface of the control section 3 of the endoscope 1 by setting the first and second operation knobs 73 and 74 in a normally upwardly-facing position as shown in FIG. 1A, subsequent to washing the endoscope, with the casing 3a of the control section 3 placed in the horizontal position.

In this case, since the first water drain guide means 77a is disposed with the recesses 73a and 74a of the first and second operation knobs 73 and 74 all down, a pool of water deposited in the recesses 73a and 74a of the respective operation knobs 73 and 74 can be run along the outer surface of the casing 3a and positively drained.

Since the second water drain guide means 77b is formed with a plurality of ridges 76 provided on the lower half section of the outer periphery of the diopter adjusting ring 75 and an even smooth surface 75a provided on the upper half section of the outer periphery of the diopter adjusting ring 75 of the eyepiece section, it is possible to run deposited water smoothly along the outer periphery of the ring 75 and drain.

The third water drain guide means 77c is formed with the grooved surface 78a provided on the lower surface side and a non-grooved smooth surface 78b on the upper surface side of the grip section 71, making it possible to run remaining water smoothly off and along the outer surface of the grip section 71 and drain.

Since the first, second and third water drain guide means 77a, 77b and 77c are mounted in at least one uniformly oriented, mount direction of the endoscope body, the endoscope 1 once being washed can be fully drained such that remaining water on the respective component parts, such as the first operation knob 73, second operation knob 74, diopter adjusting ring 75 and grip section 71, all run in the same direction through the water drain guide means 77a to 77c.

For this reason, the endoscope body, after being washed can be water-drained and dried, effectively, in a shortened period of time, effectively preventing the re-contamination of the endoscope 1 by various germs which may be multiplied on pools of water on the outer surface of the endoscope 1.

Figure 9:
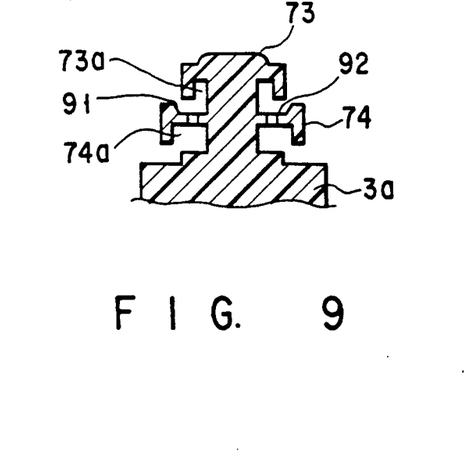
FIG. 9 is a longitudinal cross-sectional view showing a first variant of the present invention.

The present invention is not restricted to the aforementioned respective embodiment only. In the case where a recess 91 is provided upwardly on the upper surface of a second operation knob 74 as shown, for example, in FIG. 9, water drain holes 92 may be provided on the inner bottom of the recess 91 so as to enable water which is deposited on the recess bottom to be drained.

Figure 10:
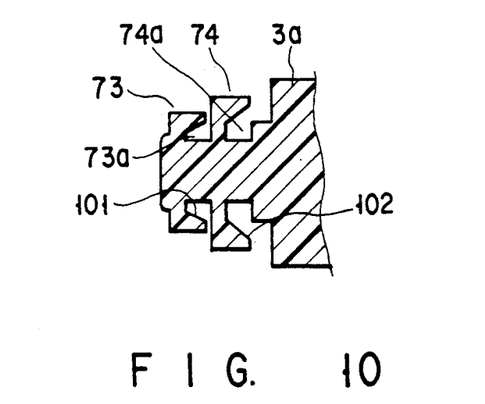
FIG. 10 is a longitudinal view showing a second variant of the present invention.

Further, in the case where the endoscope 1, after being washed, has its body placed in a vertical position, recesses 73a and 74a may be provided at first and second operation knobs 73a and 74a, respectively, with taper guide surfaces 101 and 102 formed on the inner wall of the recesses 73a and 74a as shown in FIG. 10. In this arrangement, the taper guide surfaces 101 and 102 serve as water drain surfaces for draining the water therealong.

Figure 11:
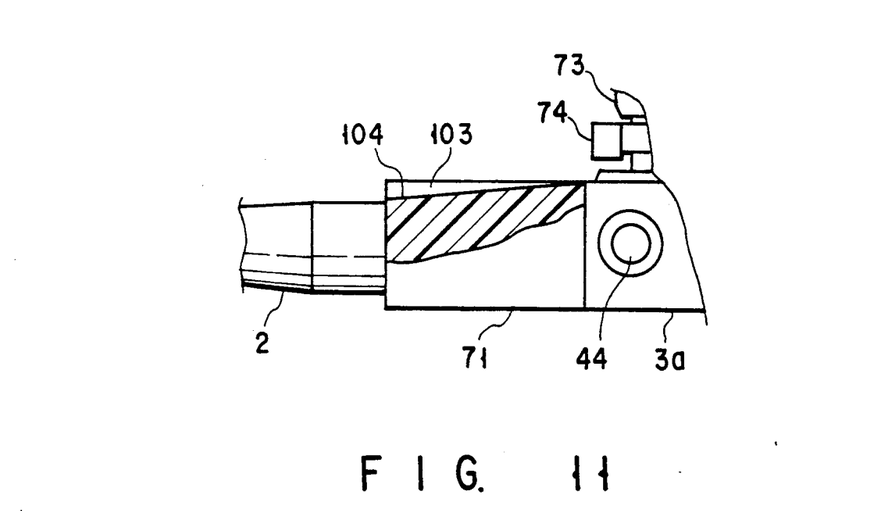
FIG. 11 is a longitudinal view showing a third variant of the present invention.

As shown in FIG. 11, a taper water drain guide surface 104 may be formed on the inner bottom surface of a slippage preventing groove 103 so that water deposited in the groove can be run along the surface 104 and drained.

A disposable endoscope may be employed so that a new endoscope can be used each time an endoscopic examination is complete. It is thus possible to positively prevent the infection of a disease from individual to individual through the use of such an endoscope.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An endoscope having a body which, when water-washed, dries in a brief period of time to positively prevent contamination of the endoscope which may be caused by germs in a pool of water on a surface of the endoscope, the endoscope comprising:

a control section positioned on an operator side;

operation knob means projecting from the control section and having a plurality of recesses on an outer surface thereof;

an insertion section insertable into at least one of a human body cavity and a duct for medically treating the at least one of the human body cavity and duct;

the operation knob means when operated, enabling a distal end portion of the insertion section to be bent; and wherein the operation knob means is so oriented as to have the plurality of recesses all opening substantially in one direction.

2. The endoscope according to claim 1, wherein:

the operating knob means has a hand grip section positioned at the control section; and the endoscope further comprises:

a water drain passage means that is arranged such that, when the endoscope body is set in a normal state, the operation knob means has a slippage-prevention uneven surface on a lower surface side of the grip section and an even smooth surface on an upper surface side of the grip section.

3. The endoscope according to claim 1, wherein:

the operation knob means has an operation knob for enabling bending of the distal end portion of the insertion section, said operation knob having a recess at an inner surface of a knob body thereof; and a water drain passage means for guiding a wash water away from the operation knob is arranged such that, after the endoscope body has been washed, the water drain passage means has a taper-like water drain passage surface at an inner wall of the operation knob when the control section is vertically positioned.

4. The endoscope according to claim 1, wherein:

the operation knob means includes an operation knob for enabling bending of the distal end portion of the insertion section, the operation knob having a recess at an inner surface of a knob body; and the endoscope further comprising:

a water drain passage means for draining a wash water for the operation knob, said water drain passage means being arranged such that, after the endoscope body is washed, the water drain passage means has a taper-like water drain passage face at an inner wall of the operation knob when the control section is vertically positioned.

5. The endoscope according to claim 1, wherein:

the operation knob means has a hand grip section at the control section; and the endoscope comprises:

a water drain passage means on said operation knob means for draining a wash water from the operation knob means, said water drain passage means being arranged such that, with the endoscope body set in a normal state, the water drain passage means has an uneven grooved, slippage-prevention section at an upper surface of the hand grip section of the operation knob means and a taper-like water drain passage surface formed in an inner bottom portion of the grooved slippage-prevention section to allow the wash water which is deposited in the grooved slippage prevention section to run off and drain into the water drain guide passage means.

6. The endoscope according to claim 1, further comprising:

a casing for the control section;

a switching valve mounted at the casing, the switching valve having:

a cylinder fixedly held in place such that the cylinder is insertable into a mount hole provided in the casing:

a cylinder connector fixed around an outer periphery of the casing at a marginal edge of the mount hole;

a button unit detachably mounted on the cylinder connector; and a tube passage washing unit mount connector mounted around an outer periphery of the cylinder connector at a position outside the casing and having a tube passage washing unit so mounted on the tube passage washing unit mount connector as to be detachable from the button unit.

7. An endoscope having a body which, when water-washed, dries in a brief period of time to positively prevent contamination of the endoscope which may be caused by germs in a pool of water on a surface of the endoscope, the endoscope comprising:

a control section positioned on an operator side;

operation knob means projecting from the control section and having a plurality of recesses on an outer surface thereof;

an insertion section insertable into at least one of a human body cavity and a duct for medically treating the at least one of the human body cavity and duct;

the operation knob means when operated, enabling a distal end portion of the insertion section to be bent; and a water drain passage means formed in the operation knob means for allowing water which is deposited on the operation knob means to be drained away from the operation knob means after the endoscope is water-washed.

8. The endoscope according to claim 7, wherein the operation knob means includes:

a first operation knob for enabling a bending of the distal end portion of the insertion section in one of a right and a left-hand direction, said first operation knob having a recess at an inner surface of a first knob body to form at least a first portion of the water drain passage mans;

a second operation knob for enabling a bending of the distal end portion of the insertion section in at least one of an up and a down direction, said second operation knob having recess at an inner surface of a second knob body to form at least a second portion of the water drain passage means; and the water drain passage means guiding a washing water from the recesses of the first and second operational knobs, said water drain passage means being arranged such that, after the endoscope body has been washed, the recesses of the first and second operation knobs are placed in a downwardly-facing direction when the control section is horizontally located with the first and second operation knobs set in a normally upward state.

9. The endoscope according to claim 8, wherein:

the second operation knob has a recess provided as a cavity in a surface of the second knob body; and the water drain passage means further includes water drain holes formed in an inner bottom portion of the recess of the second operation knob.

10. An endoscope comprising:

a control section on an operator side;

a plurality of members projecting at the control section;

an insertion section insertable into at least one of a human body cavity and a duct for medically treating the at least one of the human body cavity and duct;

a water drain guide means positioned at the respective members projecting at the control section, said water draining guide means being arranged in at least one uniformly oriented direction of the control section so that, after an endoscope body has been washed, said water drain guide means guides water deposited on the respective projecting members in a direction to run along a surface of each of the respective projecting members and to drain therefrom; and wherein one of the plurality of projecting members includes an eyepiece section for viewing an observation image at the endoscope body, said eyepiece section having a cylindrical diopter adjusting member rotatably mounted on the eyepiece section; and the water drain guide means is arranged such that, when the endoscope body is set in a normal position, the water drain guide means has plurality of slippage prevention ridges only at a lower half portion of an outer periphery of the diopter adjusting member and an even smooth surface at an upper half portion of the outer periphery of the diopter adjusting member.

11. An endoscope comprising:

a control section on an operator side;

a plurality of members projecting at the control section;

an insertion section insertable into at least one of a human body cavity and a duct for medically treating the at least one of the human body cavity and duct;

a water drain guide means positioned at the respective members projecting at the control section, said water draining guide means being arranged in at least one uniformly oriented direction of the control section so that, after an endoscope body has been washed, said water drain guide means guides water deposited on the respective projecting members in a direction to run along a surface of each of the respective projecting members and to drain therefrom; and wherein at least one of the members projecting at the control section has an operation knob means for enabling a distal end portion of the insertion section to bend the operation knob means having a recess on an inner surface of a knob body; and wherein:

the water drain guide means is arranged such that after the endoscope body has been washed, the recess of the operation knob means is placed in a downwardly-facing direction when the control section is horizontally located with the operation knob means set in a normally upward state;

the operation knob means including:

a first operation knob for controlling a bending of the distal end portion of the insertion section in one of a right and a left hand direction;

a second operation knob for enabling bending of the distal end portion of the insertion section in one of an up and a down direction; and said first and second knobs respectively having a recess at an inner surface of a respective knob body thereof, said second operation knob having said recess thereof provided as a cavity in a surface of the knob body thereof;

the water drain guide means is further arranged such that, after an endoscope body has been washed, the recesses of the first and second operation knobs are placed in a downwardly-facing direction when the control section is horizontally located with the operation knob means set in a normally upward state; and the water drain guide means has water drain holes in an inner bottom portion of the recess.

12. An endoscope comprising:

a control section on an operator side;

a plurality of projecting members projecting at the control section;

an insertion section insertable into at least one of a human body cavity and a duct for medically treating the at least one of the human body cavity and duct;

a water drain guide means positioned at the respective projecting members of the control section, said water drain guide means being arranged in at least one uniformly oriented direction of the control section so that, after an endoscope body has been washed, the water drain guide means guides water deposited on the respective projecting members in a direction to run along a surface of each of the respective projecting members and to drain therefrom; and wherein:

at least one of the projecting members projecting at the control section has an operation knob means for enabling a bending of the distal end portion of the insertion section;

said operation knob means having a recess at an inner surface of a knob body thereof;

said at least one projecting member further including:
   an eyepiece section for viewing an observation image at the endoscope body;
   a diopter adjusting member rotatably mounted on the eyepiece section for adjusting a diopter of the eyepiece section; and
   a hand grip section at the control section;

the water drain guide means being arranged such that, after the endoscope body has been washed, the recess of the operation knob body is placed in a downwardly-facing direction when the control section is horizontally located with the operation knob set in a normally upward state, the water drain guide means further having:
   a slippage-prevention uneven surface only at a lower half portion of an outer periphery of the diopter adjusting member;
   an even smooth surface at an upper half portion of the diopter adjusting member;
   an uneven slippage-prevention surface at a lower surface side of the hand grip section; and
   an even smooth surface at an upper side of the hand grip section.

* * * * *